United States Patent [19]

Carlock

[11] 4,185,038
[45] Jan. 22, 1980

[54] HYDROFORMYLATION CATALYSTS CONTAINING RHODIUM (I) OR IRIDIUM (I) CHEMICALLY BOUND DIRECTLY TO INORGANIC POLYMERS

[75] Inventor: John T. Carlock, Ponca City, Okla.

[73] Assignee: Conoco, Inc., Ponca City, Okla.

[21] Appl. No.: 924,598

[22] Filed: Jul. 14, 1978

[51] Int. Cl.$^2$ ............................................. C07C 45/08
[52] U.S. Cl. ............................................. 260/604 HF
[58] Field of Search ................ 260/604 HF; 568/909

[56] References Cited

U.S. PATENT DOCUMENTS

| | | | |
|---|---|---|---|
| 3,487,112 | 12/1969 | Paulik et al. | 260/604 HF |
| 3,557,219 | 1/1971 | Kehoe | 260/604 HF |
| 3,980,583 | 9/1976 | Mitchell | 260/604 HF |
| 3,989,759 | 11/1976 | Richfield | 260/604 HF |

Primary Examiner—Werren B. Lone

Attorney, Agent, or Firm—Cortlan R. Schupbach, Jr.

[57] ABSTRACT

Rhodium (I) and Iridium compounds covalently bound directly to inorganic oxide polymers such as silica gel, alumina, silica-titania, aluminosilicates and open-lattice clays are air-stable and have high hydroformylation activity converting all classes of olefins to aldehydes under hydrogen/carbon monoxide atmospheres at pressures of from about 100 to 1500 psig and about 90° C. to about 150° C. The catalysts have the structure

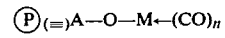

wherein A is silica, titanium alumina, M is rhodium or iridium, n is 2 or 3, respectively, and Ⓟ is an inorganic oxide polymer. The catalyst is also effective to hydrogenate the resulting aldehyde to alcohols under the same conditions and a hydrogen atmosphere.

8 Claims, No Drawings

HYDROFORMYLATION CATALYSTS CONTAINING RHODIUM (I) OR IRIDIUM (I) CHEMICALLY BOUND DIRECTLY TO INORGANIC POLYMERS

This invention relates to the hydroformylation (or oxo) activity of rhodium (I) compounds covalently bound directly to inorganic oxide polymers. More particularly, this invention relates to the oxo activity of rhodium (I) compounds or compounds capable of being reduced to rhodium (I) compounds covalently bound to inorganic oxide polymers with the capability of further hydrogenating the hydroformylation reaction product to alcohol.

The hydroformylation of terminal (or alpha) olefins is known in by certain homogenous rhodium catalysts in the art. Representative examples of references describing rhodium catalysts used in hydroformylation reactions and reaction conditions necessary are found in U.S. Pat. Nos. 3,917,661; 3,907,847; 3,821,311; 3,499,932; 3,527,809; 3,825,601; 3,948,999; and 3,984,478. Literature references of polymer-bound catalysts include *Tetrahedron Letters*, 1971 (50) 478790, Grubbs et al, Journal of Macrmol. Sci. Chem, 1973 (5) 104763, *Inorg. Chem Acta*, 1975, 12 (1), 15–21, Grubbs et al., *Polym.* Prepr. Acs *Div. Polymer Chem.*, 1972, 13 (12), 828-32. While these references are not exhaustive of the art, they appear to be representative of hydroformylation in the current state of the art. However, these catalysts and reactions are generally very poor when used with internal olefins when the catalysts are dissolved in the reaction mixture, said catalysts being difficult to recover. In addition, these materials usually employ Group V ligands such as phosphines, phosphites, organo-arsines, and organoantimony compounds which are very toxic. Recovery of the catalyst is important since these metals are extremely expensive and the product cost rises sharply with each percentage drop in metal recovery from a previous reaction.

Hydroformylation is a reaction which converts olefins "equivalent to alkenes for the purposes of this specification and claims" to aldehydes such as shown in the formula below: $RC\!=\!CR \rightarrow R\text{-}CH\text{-}CR\text{-}CHO$, wherein R is hydrogen or an alkyl. Usually the hydroformylation procedure is followed by the hydrogenation of aldehydes to produce alcohol. However, the hydrogenation procedure is relatively simple and can be carried out by any one of several well-known means. In this procedure of converting olefins to alcohols the most difficult and least efficient step is the initial hydroformylation conversion of olefins to aldehydes. In the art cited above, such conversions have been accomplished but only using catalysts which are difficult to recover and in some cases are extremely toxic.

In addition to the references above described, rhodium catalysts supported on chemically modified polymeric inorganic oxides are known in the art. The types of chemical modifications performed on the polymeric inorganic oxides necessary to attach a rhodium complex is illustrated by U.S. Pat. Nos. 3,890,583; 3,937,742; British Pat. Nos. 1,372,189; and 1,275,733. Additional references can be found in German Offengungsschrift Nos. 2,607,827 and 2,550,660. In addition, the literature contains many references which relate to this subject. Representative of these but not exhaustive are Conan et al in the *Journal of Molecular Catalysis*, 1, 375, (1976). Allum et al, *Journal of Organo Metallic Chemistry*, 87, 203 (1975), and Hancock et al Catal Proc. Int. Symp., 361 (1974). British Pat. No. 1,236,616 teaches reacting a resin with a soluble metal coordination compound and reducing the bound metal to a lower valence by using a reducing agent. The reference does not deal with inorganic polymers.

The catalyst described in these patents and publications all employ a chemical modification of the substrate, either through silylation with air sensitive silica-halogens or silica ortho formates containing an alkyl linkage at the end of which is a Group V triphenyl ligand. Others have modified the polymer with chlorophosphines to covalently bond phosphorus ligands to the substrate through the esterification of surface hydroxyl groups. These procedures are costly and difficult in implementation in that they employ toxic air and moisture sensitive intermediates which are not commercially available. The catalysts so produced are both air and moisture sensitive as well as inactive in the hydroformylation of internal olefins.

It would therefore be of great benefit to provide a catalyst bonded to an inorganic oxide polymer which has high levels of activity for the conversion of olefins, both primary and internal to aldehydes (hydroformylation) employs non-toxic material and is readily recovered. In addition, lack of sensitivity to air would be of great benefit.

It is therefore an object of the present invention to provide a method in catalyst for hydroformylation and hydrogenation reactions, said catalyst being recoverable and reuseable. Other objects will become apparent to those skilled in this art as the description proceeds.

It has now been discovered according to the present invention that a catalyst having the general formula $\text{\textcircled{P}}(\equiv)\,A\!-\!O\!-\!M\!\leftarrow\!CO_n$ wherein M is rhodium and iridium, A is silica, titanium, or aluminum, n is 2 or 3, and $\text{\textcircled{P}}$ is an inorganic oxide polymer, is an effective catalyst for the hydroformylation conversion of olefins to aldehydes under carbon monoxide/hydrogen atmospheres. The catalysts are effective under conversion conditions wherein the temperature ranges from about 90° C. to about 150° C. and pressures range from about 100 to about 3500 pounds per square inch gauge (psig). Hydroformylation occurs when the atmosphere is comprised of carbon monoxide and hydrogen, and hydrogenation will occur under the same conditions when the atmosphere is changed to essentially pure hydrogen.

The symbol $(\equiv)$ indicates that either two or three bonds may be present depending on the valency of the metal.

Higher temperatures are possible as the pressure exceeds about 2500 psig. Pressures can range up to about 3500 psig limited usually by reactor material considerations. High temperatures without sufficient pressure will yield an inefficient process.

Hydroformylation (or oxo) reactions are carried out in the presence of mixtures of hydrogen and carbon monoxide. The reaction required 1 mole of carbon monoxide for each mole of olefin reacted. Normally the ratio of hydrogen to carbon monoxide will range from about 1:100 to about 100:1 respectively although from about 80:20 to about 20:80 respectively is preferred, and from about 60:40 to about 50:50 respectively is more preferred and 50:50 respectively is most preferred.

The inorganic oxide polymer to which the active rhodium catalyst complex is bonded are inorganic oxide polymers such as silica gel, alumina, silica titania, open lattice clays and crystalline alumino silicates. Representative examples of suitable materials are aluminas such as CATAPAL and DISPAL aluminas, trademark of and sold by Continental Oil Company, titanias, such as RF30, RF31, and RF33 titanias, trademark of and sold by G&W Natural Resources Group; and Zirconiums such as ZR-0304, trademark of and sold by Harshaw chemical Co. (Cleveland, Ohio). It must be realized that these materials are not exhaustive of those useful in the instant invention.

The instant invention employs the reaction of either a halogen-containing rhodium (I) or iridium (I) complex where halogen-containing rhodium compounds of higher oxidation states are reacted with the surface hydroxyl groups of various inorganic polymeric oxides. The metal atom bonds directly to the surface of the inorganic support, thus forming a stable oxygen-metal bond. The reaction is general but is specifically illustrated with reference to equation 1 below.

When rhodium and iridium of higher oxidation states are utilized, the rhodium or iridium atom after the initial anchoring reaction can be reduced with the use of a reducing agent such as sodium borohydride solution to a +1 oxidation state. Again, the reaction is general but is specifically illustrated in formula II below.

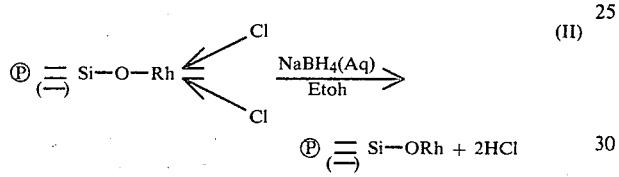

Representative examples of other reducing agents useful in the reduction of rhodium materials of higher oxidation states are potassium borohydride.

It is apparent that many commercially available rhodium compounds or complexes can be utilized in the process of the instant invention. Representative of, but not exhaustive of, these materials are the following rhodium-halogen complexes:

| $RhCl_3$ | $ClRh(PPh)_3$ | $IrCl_3$ | $[Ir(CO)_3Cl]_x$ |
|---|---|---|---|
| $RhBR_3$ | $BrPh(PPh)_3$ | $IrBr_3$ | |
| $RhI_3$ | $(ClRh(CO)_2)_2$ | $IrI_3$ | |

Thus it is apparent that the catalysts of the instant invention are easily synthesized from commercially available compounds. These catalysts do not require toxic air and moisture sensitive intermediates. These catalysts are air and moisture stable and have the central metal (I) atom bonded directly through surface hydroxyls to the inorganic polymeric oxide. In addition, these catalysts are active in hydroformylation and hydrogenation reactions employing internal olefins and readily isomerized internal double bonds to give a product containing a significantly higher percentage of linear normal aldehydes, and after hydrogenation, normal alcohols. Thus, in distinct contrast, the most rhodium-containing hydroformylation catalyst, the catalysts of the instant invention do not require special handling techniques once formulated nor do they contain undesirable group V ligands.

In addition, the inorganic oxide polymers to which the rhodium complex is bound does not require swelling solvent since catalyst access to the entire reaction mixture is possible by the basic structure of the catalyst itself. However, the use of a solvent would not effect the efficiency of the reaction and may well be desirable in certain processes because of handling considerations. However, it is emphasized that a solvent is not critical to the instant invention. Representative examples of suitable solvents useful for the instant invention are tetrahydrofuran, benzene, toluene, xylene, acetophenone and dimethylformamide.

The invention is more concretely described with reference to the examples below wherein all parts and percentages are by weight unless otherwise specified. The examples are provided for the purpose of illustrating the present invention and not for limiting it.

In all examples carried out, all olefins employed were pretreated by percolation through a 30×1 centimeter silica gel column. All synthetic operations and transfers were carried out under an inert atmosphere. The silica gel used in catalyst synthesis was calcined at 650° C. for 24 hours prior to use. All other reagents were used as commercially purchased items. While specific quantities of rhodium content were used in the catalyst illustrated, significantly higher rhodium percentages can be achieved by using larger quantities of the beginning rhodium compound. Methods of catalyst preparation are shown as well as an illustration of recovery of the catalyst by simple olefin air filtration. Chemical analysis was performed by gas liquid chromatography, infared spectroscopy and X-ray fluorescence methodology.

EXAMPLE 1

Silica gel (calcined at 650° for 48 hours, Grace Chemical Company, grade 12, 28–200 mesh) in the amount of 25 grams is added to 30 ml of absolute ethanol in a flame dried reaction vessel. This method is completely described in Takahashi et al, *Journal of Americal Chemical Society*, 97, 7489 (1975), Acres et al, *Journal of Catalysis*, 6, 139 (1967). To the solution was added 0.85 grams of rhodium trichloride.3H$_2$O and the mixture stirred and refluxed under a dry argon atmosphere for 3 hours. This mixture was then poured onto a fritted glass filter, filtered, and then washed on the filtered surface with three 30 ml portions of absolute ethanol.

After washing, the dark brown treated silica gel was added to 100 ml of absolute ethanol and reduced with 5 ml of 12% sodium borohydride solution which was slowly added over a 15 minute period with rapid stirring. The treated silica gel immediately turned black and after an additional stirring period of 30 minutes was washed on a fritted glass filter with five 150 ml portions of ethanol and eight 150 portions of distilled water. The compound was dried under vacuum for 12 hours. Rhodium and chloride analysis revealed 0.11% rhodium and less than 0.01% chlorine present. Spectroscopic analysis of the product indicated the rhodium to be in a +1 oxidation state supportive of a catalyst structure having the formula

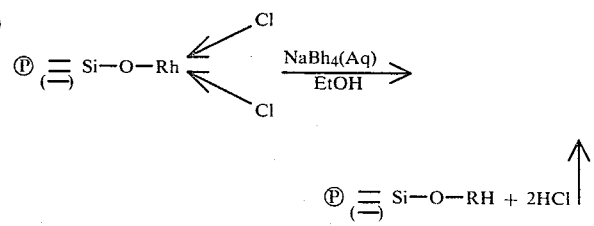

EXAMPLE 2

Freshly calcined (650° C. for 48 hours) silica gel (Grace Chemical Company, grade 12, 28–200 mesh) in the amount of 21 grams was added to a flame dried vessel containing 50 ml of anhydrous tetrahydrofuran (THF) and ½ gram of $[Rh(CO)_2Cl]_2$. This mixture was stirred for 72 hours under a dry argon atmosphere. The product was filtered, extracted with dry benzene for 10 hours, and dried under vacuum for 12 hours. Chemical analysis indicated 1.2% rhodium and 0.11% chlorine present. The molecular structure was derived which is indicated below.

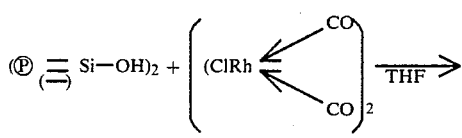

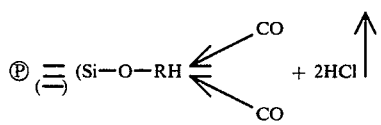

EXAMPLE 3

The catalyst prepared in Example 1 (1 gram) was charged into an autoclave with 35 grams of 7-tetradecene. The autoclave was capped, sparged 3 times to 500 psig with a 1:1 hydrogen, carbon monoxide mixture, and quickly heated to 120° C. At this temperature the 1:1 hydrogen carbon monoxide gas pressure was adjusted to 950 psig. After 415 minutes of reaction time, GLC chemical analysis of the reaction mixture showed a 90.5% conversion to $C_{15}$ aldehydes of which product 17.1% was n-pentadecanal.

EXAMPLE 4

The catalyst was recovered from Example 3 by open air filtration and recharged into an autoclave with 35 grams of 7-tetradecene. The reaction was then carried out identically as described in Example 3 except that the maximum temperature was 135° C. After 12¼ hours reaction time analysis revealed a 50.8 conversion of $C_{14}$ olefin to $C_{15}$ aldehydes. Of this product about 38.8% was identified as n-pentadecanal. It is believed that the low conversion rate is indicative of a high reaction temperature at the pressure used resulting in partial catalyst deactivation.

EXAMPLE 5

A catalyst as prepared and described in Example 2 (1.5 grams) was charged into an autoclave with 35 grams of 7-tetradecene and the reaction carried out exactly as described in Example 3. After 180 minutes of reaction time, analysis indicated an 85.5% conversion of $C_{14}$ olefin to $C_{15}$ aldehydes. 10.6% of the product was n-pentadecanal.

EXAMPLE 6

The catalyst from Example 5 was recovered by filtration and recharged into an autoclave with 35 grams of 1-dodecene. The reaction was carried out identical to that for Example 3 except that a maximum temperature of 100° C. was used. After 12 hours of reaction analysis of the reaction mixture revealed 49.3% conversion of $C_{12}$ olefins to $C_{13}$ aldehydes having a normal to isomerized ratio of 1.3. The low conversion rate observed in this example is indicative of a reaction temperature which is too low to be efficient.

The results of these experiments as well as the rhodium elution noted in parts per million by ashing the liquid product and obtaining X-ray fluorescence spectra on the ash. The results are set forth in tabular form in Table I.

TABLE I

| Seq. No. | Catalyst | Reactant | Product | Hydroformylation Reaction % Conversion/ Hrs. Time | °C./PSIG | % Linear RCHO | Rh Elution (PPM) |
| --- | --- | --- | --- | --- | --- | --- | --- |
| 3 | Ex 1 | 7-tetradecene | $C_{15}$ aldehydes | 90.5/6.9 | 120°/950 | 17.1 | 26 |
| 4 | Ex 1 | 7-tetradecene | $C_{15}$ aldehydes | 50.8/12.25 | 135°/950 | 38.7 | <5 |
| 5 | Ex 2 | 7-tetradecene | $C_{15}$ aldehydes | 85.5/3.0 | 120°/950 | 9.1 | — |
| 6 | Ex 2 | 1-dodecene | $C_{13}$ aldehydes | 49.3/12.0 | 100°/950 | 56.5 | 12 |

The catalysts of the instant invention are also useful for the hydrogenation of unsaturated organic compounds. This facility of the catalyst is shown in the examples below utilizing the catalysts prepared in Examples 1 and 2.

EXAMPLE 7

The catalyst as prepared in Example 2 (1 gram) was charged into an autoclave containing 35 grams of 7-tetradecene and reacted under the oxo conditions specified in Example 3. Complete conversion of the olefin to aldehyde had been achieved, gas supply was changed from hydrogen carbon monoxide to pure hydrogen and the system thoroughly sparged 15 times to 900 psig hydrogen. The reactor temperature was maintained at 120° C. and the hydrogen gas pressure adjusted to 950 psig at this temperature. After 4.5 hours of reaction time, analysis of the reaction mixture revealed a 96% conversion of $C_{15}$ aldehydes to $C_{15}$ alcohols.

EXAMPLE 8

The catalyst was recovered from Example 7 reaction by open air filtration and recharged into an autoclave with 35 grams of 7-tetradecene. The reaction was then carried out identically with that described in Example 7 except that the hydrogen gas pressure was employed throughout the entire reaction duration and the gas pressure was maintained at 600 psig hydrogen. After 15 minutes of reaction time, chemical analysis of the reaction mixture revealed a 100% conversion of the olefin to n-tetradecane.

EXAMPLE 9

The catalyst was recovered from the Example 8 reaction and charged into a reactor with 35 grams of 1,7-octadiene. The reaction was carried out identically with that described in Example 8 except that the reactor temperature was reduced to 110° C. and the gas pressure reduced to 500 psig hydrogen. After 13 minutes of reaction time, chemical analysis of the reaction mixture revealed a 100% conversion of the diene to n-octane.

time chemical analysis reveals a significant conversion of 7-tetradecene to $C_{15}$ aldehydes.

TABLE II

| Seq. No. | Catalyst | Reactant | Product | Hydrogenation % Conversion/ Hrs. Time | °C./PSIG | Rh Elution (PPM) |
|---|---|---|---|---|---|---|
| 7 | Ex 2 | 7-tetradecene | $C_{15}$ aldehydes | 95%/5.0 | 120°/950 | — |
| 7 | Ex 2 | $C_{15}$ aldehydes | $C_{15}$ alcohols | 96%/4.5 | 120°/950 | — |
| 8 | Ex 2 | 7-tetradecene | n-tetradecane | 100%/0.250 | 120°/600 | 0.27 |
| 9 | Ex 2 | 1,7-octadiene | n-octane | 100%/0.216 | 110°/500 | <2 |
| 10 | Ex 2 | Benzene | Cyclohexane | 100%/0.301 | 110°/500 | <2 |
| 11 | Ex 2 | Methyl acrylate | Methyl propinate | 100%/0.416 | 110°/320 | <1 |
| 12 | Ex 1 | Benzene | Cyclohexane | 84%/2.96 | 110°/900 | <8 |

EXAMPLE 10

The catalyst was recovered from the example 9 reaction and charged into a reactor with 35 grams of benzene. The reaction conditions were identical with those carried out in Example 9. After 31 minutes of reaction time, chemical analysis of the reaction mixture revealed a 100% conversion of the benzene to cyclohexane.

EXAMPLE 11

The catalyst was recovered from the Example 10 reaction and charged into a reactor with 35 grams of methyl acrylate. The action conditions were the same as those described in Example 10 except that the gas pressure was reduced to 320 psig hydrogen. After 25 minutes of reaction time, chemical analysis of the reaction mixture revealed a 100% conversion of methyl acrylate to methyl propionate.

EXAMPLE 12

The Example 1 catalyst (1 gram) was charged into an autoclave followed by 35 grams of benzene. The reactor was sparged 3 times to 500 psig hydrogen and heated to 100° C. At this temperature the gas pressure was adjusted to 500 psig. After 70 minutes of reaction time, vapor phase chromatography revealed a 15% conversion of benzene to cyclohexane. The reactor temperature was then raised to 110° C. and the gas pressure adjusted to 900 psig hydrogen at this temperature. After an additional reaction of 108 minutes, analysis of the reaction mixture revealed that 84% conversion of benzene to cyclohexane. Rhodium elution was obtained using X-ray fluorescense as previously described.

The results of the hydrogenation reactions using the catalysts in the instant are set forth in Table 2 below.

EXAMPLE 13

Twenty-five grams of calcined (as per Example 1) Grace Grade 12 silica gel is added to 25 ml of absolute ethanol in a flame-dried flask. One gram of hydrated iridium trichloride is added and the mixture is stirred and refluxed for sufficient time to form the catalyst and is then purified as set forth in Example 1.

EXAMPLE 14

Two grams of the catalyst described in Example 13 swollen to 20 ml benzene is charged into an autoclave with 35 grams of 7-tetradecene. The reactor is purged with a (1:1) $H_2/CO$ mixture and heated quickly to 120° C. at which temperature the 1:1 $H_2CO$ gas pressure is reduced to 1000 psig. After an appropriate period of time chemical analysis reveals a significant conversion of 7-tetradecene to $C_{15}$ aldehydes.

The instant invention thus provides a method for converting olefins both primary and internal to aldehydes, and if desired, further to alcohols while using an inorganic oxide polymer bound rhodium (I) iridium (I) containing catalyst which has no toxic group V ligands, yet is capable of efficient conversion of internal and primary olefins to aldehydes. In addition, the method of the instant invention requires no special handling techniques under inert atmosphere, and thus is highly desirable from a commercial viewpoint. Catalyst recovery is excellent and subsequent reactions can be carried out with little loss of conversion.

While certain embodiments and details have been shown for the purpose of illustrating this invention, it will be apparent to those skilled in this art that various changes and modifications may be made herein without departing from the spirit or the scope of the invention.

I claim:

1. A method for converting olefins to aldehydes comprising converting said olefins in the presence of a catalyst of the general formula ⓅⒾ A—O—M←(CO)$_n$ at temperatures of from about 90° C. to about 150° C. and pressures of from about 100 to about 1500 psig of an atmosphere of carbon monoxide and hydrogen, wherein A is silicon, titanium or aluminum, M is rhodium or iridium, n is 0 to 2, respectively, and P is an inorganic oxide polymer selected from the group consisting of silica gel, alumina titania-alumina, open lattice clays, and crystalline alumino silicates.

2. A method as described in claim 1 wherein M is rhodium.

3. A method as described in claim 2 wherein the carbon monoxide hydrogen atmosphere is in a ratio of from about 80:20 to 20:80 respectively.

4. A method as described in claim 3 wherein the carbon monoxide hydrogen atmosphere is replaced with essentially pure hydrogen at the completion of the hydroformylation reaction and hydrogenation is allowed to occur.

5. A method as described in claim 4 wherein primary alcohols are formed from internal olefins.

6. A method for converting olefins to aldehydes comprising converting said olefins in the presence of a catalyst at temperatures of from about 90° to about 150° C. and H/CO pressures of from about 100 to about 1500 psig, wherein the catalyst is prepared by combining halogen-containing complexes of rhodium or iridium, or mixtures of these, with inorganic polymers containing surface hydroxyl groups.

7. A method as described in claim 6 wherein the catalyst is reduced with a reducing agent before recovering the catalyst.

8. A method as described in claim 7 wherein the reducing agent is sodium borohydride, potassium borohydride and lithium borohydride.

* * * * *